US00PP26814P3

(12) United States Plant Patent
Urwin

(10) Patent No.: US PP26,814 P3
(45) Date of Patent: Jun. 7, 2016

(54) LAVENDER PLANT NAMED 'RIVERINA GURLI'

(50) Latin Name: *Lavandula hybrida*
Varietal Denomination: Riverina Gurli

(71) Applicant: Nigel Alexander Russel Urwin, Wagga Wagga (AU)

(72) Inventor: Nigel Alexander Russel Urwin, Wagga Wagga (AU)

( * ) Notice: Subject to any disclaimer, the term of this patent is extended or adjusted under 35 U.S.C. 154(b) by 245 days.

(21) Appl. No.: 13/999,861

(22) Filed: Mar. 29, 2014

(65) Prior Publication Data
US 2015/0282416 P1 Oct. 1, 2015

(51) Int. Cl.
*A01H 5/02* (2006.01)

(52) U.S. Cl.
USPC ..... Plt./445

(58) Field of Classification Search
USPC ..... Plt./445
CPC ..... A01H 5/02
See application file for complete search history.

*Primary Examiner* — Kent L Bell

(57) ABSTRACT

A new cultivar of Lavender plant named 'Riverina Gurli' that is characterized by pink-red flowers with light pink sterile bracts, a rounded overall shape and a compact habit.

1 Drawing Sheet

Botanical classification: *Lavandula hybrida.*
Variety denomination: 'Riverina Gurli'.

BACKGROUND OF THE INVENTION

The present invention relates to a new and distinct cultivar of Lavender plant botanically known as *Lavandula hybrida* and hereinafter referred to by the cultivar name 'Riverina Gurli'.

In 2004, approximately 90 Lavender plants were removed from an outdoor bed in a cultivated area of Wagga Wagga, New South Wales Australia. The outdoor bed contained many different hybrid Lavender plants. The 90 Lavender plants were grown in containers and observed in Wagga Wagga, New South Wales, Australia. 'Riverina Gurli' was discovered in 2005 as a single plant from among the 90 Lavender plants based on flower color and overall plant shape. The exact parent plants are unknown.

Asexual reproduction of the new cultivar 'Riverina Gurli' by terminal cuttings was first performed in 2005 in Wagga Wagga, New South Wales, Australia. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Lavender cultivar 'Riverina Gurli'. These traits in combination distinguish 'Riverina Gurli' as a new and distinct cultivar.

1. Lavender 'Riverina Gurli' exhibits pink-red flowers with light pink sterile bracts.
2. Lavender 'Riverina Gurli' exhibits a rounded overall shape.
3. Lavender 'Riverina Gurli' exhibits a compact habit.

The closest comparison cultivars are Lavender 'Kew Red' and Lavender 'Bella Pink' (U.S. Plant Pat. No. 12,599). 'Riverina Gurli' is different than 'Kew Red' in having a larger number of flowers, a more upright habit and pink-red colored flowers. In comparison, the flowers of 'Kew Red' are a red in color. 'Riverina Gurli' is different than 'Bella Pink' in having a more rounded shape, smaller inflorescence dimensions and pink-red colored flowers. In comparison, the flowers of 'Bella Pink' are darker purple-red in color.

BRIEF DESCRIPTION OF THE DRAWING

The accompanying photograph illustrates the distinguishing traits of Lavender 'Riverina Gurli'. The plant in the photograph shows an overall view of a 15 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Lavender cultivar named 'Riverina Gurli'. Data was collected in Wagga Wagga, New South Wales, Australia from 15 week old outdoor grown plants. The time of year was Summer in the Southern Hemisphere and the average temperature was 20 to 28° Centigrade during the day and 12 to 18° Centigrade at night. Color determinations are in accordance with The Royal Horticultural Society Colour Chart 2001 edition, except where general color terms of ordinary dictionary significance are used. The growing requirements are similar to the species. 'Riverina Gurli' has not been tested under all possible conditions and phenotypic differences may be observed with variations in environmental, climatic, and cultural conditions, however, without any variance in genotype.

Botanical classification: *Lavandula hybrida* 'Riverina Gurli'.
Use: Ornamental Perennial.
Parentage: The exact parent plants of 'Riverina Gurli' are unknown.
Vigor: Moderate.
Container size: 10 cm. and larger.

Growth habit: Upright, outwardly spreading.
Plant shape: Rounded with erect flower spikes.
Height: Average 42 cm. in height.
Width: Average 94 cm. in width.
Hardiness: −9° to 38° C.
Propagation: Terminal cuttings.
Crop time: 9 months.
Stem:
- *Branching habit*.—Free branching.
- *Number of lateral branches*.—Approximately 70.
- *Lateral branch diameter*.—4 mm. in diameter.
- *Lateral branch length*.—30 cm. in length.
- *Lateral branch strength*.—Strong.
- *Color*.—144C.
- *Pubescence*.—Lightly covered with short hairs.
- *Internode length*.—3.6 cm. between nodes.
- *Shape*.—Round.

Foliage:
- *Leaf arrangement*.—Opposite.
- *Compound or single*.—Single.
- *Quantity of leaves per lateral branch*.—24.
- *Leaf shape*.—Linear.
- *Leaf apex*.—Rounded.
- *Leaf base*.—Rounded.
- *Leaf length*.—5.1 cm. in length.
- *Leaf width*.—6.2 mm. in width.
- *Texture*.—Velvety.
- *Pubescence*.—Present.
- *Leaf margin*.—Entire.
- *Vein pattern*.—Pinnate.
- *Young leaf color* (*upper surface*).—138A.
- *Young leaf color* (*lower surface*).—138B.
- *Mature leaf color* (*upper surface*).—138A.
- *Mature leaf color* (*lower surface*).—138B.
- *Vein color* (*both surfaces*).—N144C.
- *Leaf attachment*.—Sessile.

Flower:
- *Flower arrangement*.—Terminal cylindrical spikes.
- *Inflorescence dimensions*.—4.0 cm. in length and 1.6 cm. in diameter.
- *Quantity of flowers and buds per inflorescence*.—Approximately 45.
- *Quantity of inflorescences per plant*.—Approximately 75.
- *Flowering season*.—Spring to Summer.
- *Time to flower or response time*.—4 to 6 weeks after buds form.
- *Fragrance*.—Musk scent.
- *Self-cleaning or persistent*.—Self cleaning.
- *Flower bud length*.—25 mm. in length.
- *Flower bud diameter*.—12 mm. in diameter.
- *Flower bud shape*.—Ovate.
- *Bud color*.—64C.
- *Flower aspect*.—Outward.
- *Flower shape*.—Salverform.
- *Flower dimensions*.—4 mm. in diameter and 8 mm. in height.
- *Flower longevity*.—Lasts approximately 20 to 25 days.
- *Petal arrangement*.—Rotate with five petals fused into a tube.
- *Petal shape*.—Spathulate.
- *Petal margin*.—Entire.
- *Petal apex*.—Rounded.
- *Petal texture*.—Smooth.
- *Petal dimensions*.—7 mm. in length and 2.6 mm. in width.
- *Petal color when opening* (*upper side*).—N79C.
- *Petal color when opening* (*under side*).—N79C.
- *Petal color when fully opened* (*upper side*).—N79C.
- *Petal color when fully opened* (*under side*).—N79C.

Sepals:
- *Sepal number*.—5.
- *Sepal shape*.—Linear.
- *Sepal apex*.—Acute.
- *Sepal base*.—Fused.
- *Sepal margin*.—Entire.
- *Sepal texture* (*both surfaces*).—Velvety.
- *Sepal dimensions*.—2.8 mm. in length and 1 mm. in width.
- *Sepal color* (*both surfaces*).—N187B.

Calyx:
- *Calyx shape*.—Campanulate tube.
- *Calyx dimensions*.—3 mm. in length and 1.5 mm. in diameter.

Peduncle:
- *Peduncle dimensions*.—4.5 cm. in length and 2.5 mm. in diameter.
- *Peduncle color*.—144B.
- *Peduncle strength*.—Medium.

Sterile bracts:
- *Sterile bract location*.—On top of each spike.
- *Sterile bract quantity*.—4.
- *Sterile bract shape*.—Oblanceolate.
- *Sterile bract apex*.—Rounded.
- *Sterile bract base*.—Cuneate.
- *Sterile bract margin*.—Entire, undulating.
- *Sterile bract texture* (*both surfaces*).—Velvety.
- *Sterile bract dimensions*.—3.3 cm. in length and 2.4 cm. in width.
- *Sterile bract color* (*upper side*).—N80B.
- *Sterile bract color* (*under side*).—N80B.

Fruit and seed production: Plants of the new Lavender have not been observed for fruit and seed production.

Disease and pest resistance: Plants of the new Lavender have not been observed for disease or pest resistance.

The invention claimed is:

1. A new and distinct variety of Lavender plant named 'Riverina Gurli' as described and illustrated.

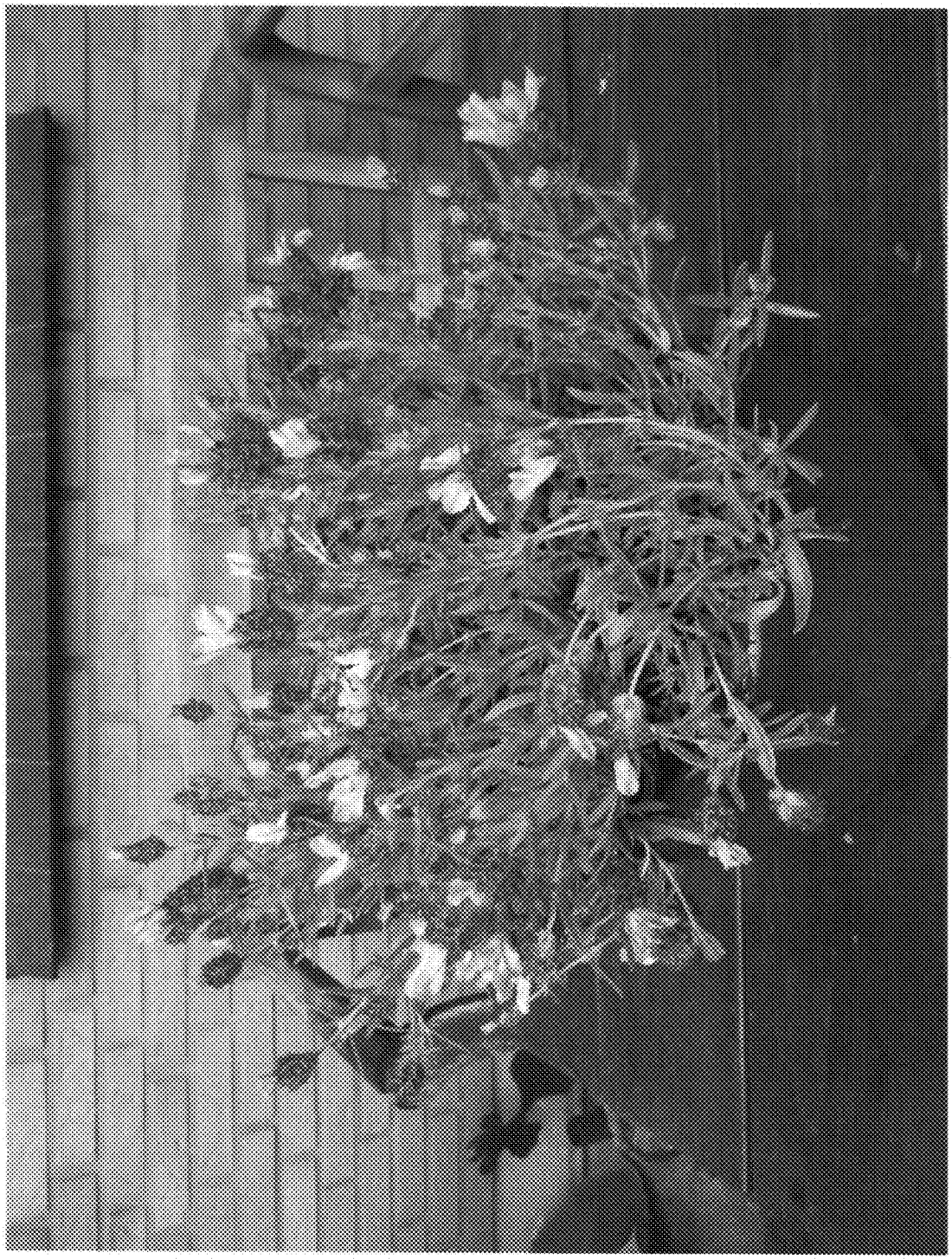

* * * * *